United States Patent [19]

Anabuki et al.

[11] 4,415,555
[45] Nov. 15, 1983

[54] COMPOSITION AND METHOD FOR TREATING IRON DEFICIENCY SYNDROME

[75] Inventors: Hitoshi Anabuki; Shigeo Miyata, both of Takamatsu, Japan

[73] Assignee: Kyowa Chemical Industry C. Ltd., Tokyo, Japan

[21] Appl. No.: 359,126

[22] Filed: Mar. 17, 1982

[30] Foreign Application Priority Data

Mar. 24, 1981 [JP] Japan .................................. 56-41723

[51] Int. Cl.³ ...................... A61K 33/26; C01B 31/24; C07F 5/06; A61K 31/295
[52] U.S. Cl. ................................ 424/147; 260/448 B; 423/419 P; 423/554; 423/594; 424/295
[58] Field of Search ............................... 424/147, 295; 260/448 B; 423/419 P, 554, 594

[56] References Cited

U.S. PATENT DOCUMENTS 3,650,704  3/1972  Kumura et al. ..................... 424/154
3,829,561  8/1974  Heinrich ............................. 424/147

Primary Examiner—Douglas W. Robinson
Attorney, Agent, or Firm—Sherman & Shalloway

[57] ABSTRACT

A composition for treating an iron deficiency disease, composed of (1) an amount, effective for treating said disease, of a compound having a hydrotalcite-like crystal structure and represented by the following formula

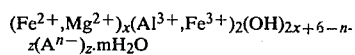

$$(Fe^{2+}, Mg^{2+})_x(Al^{3+}, Fe^{3+})_2(OH)_{2x+6-n \cdot z}(A^{n-})_z \cdot mH_2O$$

wherein $A^{n-}$ represents an anion having a valence of n, $Mg^{2+}$ is within the range of $0 \leq Mg^{2+} < x$, $Fe^{3+}$ is within the range of $0 \leq Fe^{3+} \leq 2$, x is a number represented by $1 \leq x < 20$, z is a number represented by $0 < z < 3$, and m is a number represented by $0 \leq m < 8$, and (2) a pharmaceutically acceptable diluent or carrier, and a method for treating an iron deficiency disease, which comprises orally administering an amount, effective for treating said disease, of the compound represented by the aforesaid formula.

18 Claims, 1 Drawing Figure

FIG. 1

COMPOSITION AND METHOD FOR TREATING IRON DEFICIENCY SYNDROME

This invention relates to a new agent for treating an iron deficiency syndrome, which exhibits excellent activity in the prevention and therapy of various diseases associated with iron deficiency, such as iron deficiency anemia and hypoferremia, with a long-lasting efficacy and markedly reduced side-effects; and to a method for treating the iron deficiency syndrome by using the aforesaid composition.

More specifically, this invention pertains to a composition for treating an iron deficiency disease, composed of (1) an amount, effective for treating said disease, of a compound having a hydrotalcite-like crystal structure and represented by the following formula (1)

$$(Fe^{2+}, Mg^{2+})_x(Al^{3+}, Fe^{3+})_2(OH)_{2x+6-nz}(A^{n-})_z \cdot mH_2O \quad (1)$$

wherein $A^{n-}$ represents an anion having a valence of n, $Mg^{2+}$ is within the range of $0 \leq Mg^{2+} < x$, $Fe^{3+}$ is within the range of $0 \leq Fe^{3+} < 2$, x is a number represented by $1 \leq x < 20$, z is a number represented by $0 < z < 3$ and m is a number represented by $0 \leq m < 8$, and a pharmaceutically acceptable diluent or carrier.

The invention also pertains to a method for treating an iron deficiency disease which comprises orally administering an amount effective, for treating said disease, of the compound of formula (1).

It is known that the deficiency of iron, an essential ingredient for hemoglobin synthesis in vivo, inhibits the formation of hemoglobin, and causes various anemic symptoms such as general malaise, headache, dizziness, sounding in the ears, pain at the glossal mucous membrane, reduced appetite, epigastralgia, etc. The causes of such iron deficiency include, for example, the lack of iron up-take from foods, the insufficiency of iron absorption due to abnormality or reduction of the function of the stomach and small intestine, the increased demand for iron in vivo during the rapidly growing stage of infants or during pregnancy, and the unusually increased excretion of iron during menstruation or due to bleeding by peptic ulcer or other lesions. It is difficult to make up for such iron deficiency by foods alone because the ratio of iron absorbed by eating is very low and the amount of foods that can be taken is naturally limited. It is the general practice therefore to supply iron by orally or parenterally administering various iron-containing compounds as treating agents for the prevention and therapy of an iron deficiency syndrome.

Various inorganic and organic iron-containing compounds have been used heretofore as treating agents for iron deficiency, but none of them have proved to meet the three important requirements of such treating agents, i.e. high absorption in vivo, long-lasting efficacy, and reduced side-effects.

Iron taken into the body is absorbed in the form of a ferrous ion (divalent) from the duodenum [see, for example, Nakao et al., "Shin Naikagaku Taikei" (Outline of New Internal Medicine), Diseases of Blood and Blood-Forming Organ 1, page 185, published by Nakayama Shoten, Japan], and therefore, such iron-containing compounds are desirably used in the form of an inorganic divalent iron salt such as ferrous sulfate or reduced iron (FeO). These inorganic iron salts, however, have the defect of stimulating the mucous membrane of the stomach and being likely to cause a serious gastric trouble. Since it is common that continued administration over several months is required for the treatment of iron deficiency, the aforesaid defect sets a marked restriction on the use of inorganic ferrous salts as treating agents for iron deficiency.

In order to eliminate this defect of inorganic ferrous salts for the treatment of iron deficiency, there have been used various organic acid salts of iron which do not permit dissociation of iron in an amount large enough to cause troubles to the mucous membranes of the stomach, and can be ionized in the duodenum which is the site of iron absorption. Examples of such organic acid salts of iron are iron fumarate, iron succinate and iron gluconate. Although these organic acid salts of iron have the advantage of obviating gastric troubles to some extent, they suffer the new defect that the amount of iron absorbed and utilized decreases. This defect makes it necessary to administer these compounds in large amounts. In addition, since the ratio of iron to be absorbed generally decreases with increasing amount of iron administered at a time, the aforesaid need for administration of large amounts makes it difficult to essentially avoid the gastric troubles.

We have undertaken extensive investigations in order to provide an iron deficiency treating agent of a new type which is free from the defects of the conventional agents for treating iron deficiency. These investigations have led to the discovery that the compound of formula (1) having a hydrotalcite-like crystal structure exhibits excellent activity in the prevention and therapy of an iron deficiency syndrome with a long-lasting efficacy, extremely low toxicity ($LD_{50}$) and reduced side-effects as well as a high absorption of iron in vivo.

The pharmacological mechanism by which the iron deficiency treating agent of this invention exhibits excellent results has not yet been fully elucidated. We have observed that the compound of formula (1) is substantially insoluble in water but is soluble in gastric acid and can rapidly neutralize gastric acid to a pH of about 4 within a period on the order of several seconds to several tens of seconds; and that since the crystal surface of the compound of formula (1) is strongly charged positively, the compound (1) is adsorbed to, and stays for an extended period of time on, the walls of the stomach and duodenum which are negatively charged. For this reason, unlike conventional inorganic ferrous salts such as water-soluble ferrous sulfate, the formation of a large amount of a ferrous ion at a time within the stomach which may lead to undesirable gastric troubles is not likely when the compound of formula (1) according to the invention is administered. For example, we have observed that 0.5 g of the compound of formula (1) can rapidly neutralize gastric acid to a favorable pH range of 3 to 5, and this pH is maintained for a period of about 60 minutes. Thus, the occurrence of a gastric trouble can be fully inhibited. Moreover, the compound of formula (1) stays for a long period of time in the stomach or duodenum and releases iron continuously to enable iron to be absorbed at a sufficient ratio with a long duration, thus eliminating the low absorption ratio of conventional organic acid salts of iron and the need to administer large amounts of such organic acid iron salts. We presume therefore that the compound of formula (1) can exhibit excellent activity and a long-lasting efficacy in the prevention and therapy of the iron deficiency syndrome while inhibiting the occurrence of gastric troubles and achieving a high iron absorption. It is to be understood, however, that the present invention is in no way limited by the aforesaid theoretical discussion of the pharmacological mechanism by which the compound of formula (1) produces the aforesaid excellent results.

It is an object of this invention to provide a new agent for treating an iron deficiency disease which exhibits excellent activity and a long-lasting efficacy in the prevention and therapy of diseases associated with the deficiency of iron, such as iron deficiency anemia, with reduced side-effects and very low toxicity.

The above and other objects and advantages of this invention will become more apparent from the following description.

The iron deficiency treating agent of this invention comprises as an active ingredient a compound having a hydrotalcite-like crystal structure and represented by the following formula (1)

wherein $A^{n-}$ represents an anion having a valence of n, $Mg^{2+}$ is within the range of $0 \leq Mg^{2+} < x$, $Fe^{3+}$ is within the range of $0 \leq Fe^{3+} < 2$, x is a number represented by $1 \leq x < 20$, preferably $2.5 \leq x < 8$, more preferably $3 \leq x \leq 6$, z is a number represented by $0 < z < 3$, preferably $1 \leq z \leq 2$, and m is a number represented by $0 \leq m < 8$.

Examples of preferred anions $A^{n-}$ include $CO_3^{2-}$, $SO_4^{2-}$, $OH^{1-}$, a tartrate anion $[(CHOHCOO)_2^{2-}]$, a gluconate anion $[(CHOH)_4CH_2OHCOO^-]$, a fumarate anion $[C_2H_2(COO)_2^{2-}]$, a succinate anion $[(CH_2COO)_2^{2-}]$, a glucronate anion $(C_5H_9O_5COO^-)$, a glycine anion $(CH_2NH_2COO^-)$, and a lactate anion $(CH_3CHOHCOO^{-1})$.

Among the compounds expressed by formula (1), those of the following formula (1)' are preferred.

(1)'

In formula (1)', x, z and m are as defined above, and it is especially preferred that x be a number represented by $2.5 \leq x < 8$, especially $3 \leq x \leq 6$, z be a number represented by $1 \leq z \leq 2$, and m be a number represented by $0 \leq m < 8$.

The active ingredient of formula (1) used in this invention has a crystal structure similar to that of hydrotalcite, and the crystal surface is strongly charged positively. The hydrotalcite-like crystal structure, as referred to in this invention, means that the compound of formula (1) shows a diffraction pattern in powder X-ray diffraction (JCPDS No. 14-191) which is substantially identical with, or very similar to, the diffraction pattern of hydrotalcite $[Mg_6Al_2(OH)_{16}CO_3 \cdot 4H_2O]$. It is observed, that when the anion $A^{n-}$ in the compound of formula (1) is other than $CO_3^{2-}$, its lattice constant $C_o$ shifts depending upon the size (ion radius) of the anion, and that the lattice constant $a_o$ decreases in inverse proportion to the content of Al in response to variations in the mole ratio of Fe:Al. The differences are slight, however.

The active ingredient of formula (1) according to this invention can be obtained as a precipitate, for example, by reacting (i) an aqueous solution of a water-soluble divalent iron salt or an aqueous solution of a water-soluble divalent iron salt and a water-soluble magnesium compound with (ii) an aqueous solution of a water-soluble aluminum compound or an aqueous solution of a water-soluble aluminum compound and a water-soluble trivalent iron salt in the presence of an alkali at a pH of, for example, at least about 6, preferably about 8 to about 12.

Since divalent iron is susceptible to oxidation to trivalent iron even in the presence of a relatively small amount of oxygen, it is preferred to remove dissolved oxygen from the starting aqueous solution as much as possible by known techniques, for example by blowing nitrogen gas or other non-oxidizing inert gases into the solution, before the reaction is carried out. It is also preferred that the reaction be carried out in an atmosphere of an inert gas substantially free from oxygen, such as nitrogen gas.

The reaction temperature can be properly chosen, and is, for example, room temperature to about 80° C. The reaction time can also be properly chosen. For example, it is about 20 minutes to about 60 minutes. Preferably, the reaction mixture after the reaction is washed with water, alcohols, etc. while minimizing contact with oxygen. When the starting solutions (i) and (ii) do not contain the anion $A^{n-}$, the reaction product may be contacted with an aqueous solution of the desired anion $A^{n-}$ to convert it to a compound having the desired anion $A^{n-}$. As required, the product is filtered and washed with water; and if desired, dried in an atmosphere of nitrogen gas or another inert gas substantially free from oxygen, and stored. The storage is preferably effected in a non-oxidizing atmosphere or in a reducing atmosphere such as hydrogen.

Examples of the water-soluble divalent iron salt used in the above reaction include ferrous sulfate, ferrous chloride, ferrous nitrate, ferrous ammonium sulfate, ferrous lactate, ferrous fumarate and ferrous oxalate.

Examples of the water-soluble magnesium salts include magnesium chloride, magnesium nitrate, magnesium sulfate, magnesium bromide, magnesium acetate, magnesium citrate, magnesium fluoride, magnesium lactate, and magnesium oxalate.

Examples of the water-soluble aluminum compound include aluminum chloride, aluminum nitrate, aluminum bromide, aluminum fluoride, aluminum sulfate, aluminum ammonium sulfate, aluminum potassium sulfate, aluminum isopropoxide, aluminum sodium sulfate, sodium aluminate, potassium aluminate and aluminum acetate.

Examples of the water-soluble trivalent iron salt include ferric chloride, ferric citrate, ferric sulfate, ferric nitrate, ferric ammonium oxalate and ferric ammonium sulfate.

In performing the above reaction, it is preferred to dissolve the above-exemplified water-soluble salts or compounds in water, for example distilled water from which dissolved oxygen has been removed by blowing a non-oxidizing inert gas such as nitrogen gas, to prepare the starting aqueous solutions (i) and (ii). To react the aqueous solutions (i) and (ii) in the presence of an alkali, the alkali may be added after the two aqueous solutions have been mixed. Alternatively, the alkali may be added to one or both of these aqueous solutions before they are mixed. The alkali used may be of such a type and amount as can maintain the pH of the reaction system at at least about 6, preferably at about 8 to about 12. Examples of such alkalies are sodium hydroxide, potassium hydroxide, ammonia gas, sodium carbonate, potassium carbonate and calcium hydroxide. Preferably, the reaction is carried out with sufficient stirring.

Where the aqueous solutions (i) and (ii) used in the aforesaid reaction do not contain the desired anion $A^{n-}$, for example a lactate anion, a fumarate anion, a glycine anion or a gluconate anion, the reaction product after the reaction may be contacted with an aqueous solution containing the anion $A^{n-}$, for example an aqueous solution of an alkali metal salt of the anion to perform ion-exchanging reaction and thereby to convert it to a compound containing the desired $A^{n-}$. Or by adding the anion $A^{n-}$ to the starting solutions (i) and/or (ii) or to the reaction system and then reacting the solutions (i) and (ii), a compound of formula (1) containing the desired anion $A^{n-}$ may be formed. The aforesaid anion exchange reaction can be carried out by mixing the reaction product with an aqueous solution of an alkali metal salt of the anion; or by filling the reaction product in a column and passing the aqueous alkali metal solution through the column.

If the pH of the reaction system is lower than about 6, the amount of divalent iron reacted abruptly decreases. If, on the other hand, the pH of the reaction system is higher than about 13, aluminum does not easily participate in the reaction. For this reason, the suitable pH of the reaction system is about 6 to about 13, preferably about 8 to about 12, especially preferably about 8 to about 11.

The compound of formula (1) according to our invention has extremely low toxicity as expressed by its $LD_{50}$ in mice (oral) of at least 7,000 mg/kg.

The compound of formula (1) is useful for preventing, curing or otherwise treating an iron deficiency syndrome in man and other animals by administering it either as such or as a composition in any desired dosage form together with pharmaceutically acceptable diluents or carriers with or without other additives or adjuvants.

Oral administration is a preferred route of administration. The dosage can be varied properly depending upon the type of the iron deficiency disease to be treated, its severity, the route of administration, the administration period, etc. In terms of the amount of the active ingredient of formula (1), the suitable dosage is, for example, about 50 to about 2,000 mg per day per adult (body weight 60 kg). Preferably, a dosage of about 50 to about 400 mg may be administered per day in one to three portions.

The iron deficiency treating agent of the invention may be in various forms, such as powders, granules, pills, tablets, capsules, suspensions and emulsions. It may also be in the form of pastes, chewing gums and drinks.

In preparing pharmaceutical compositions in these various forms, pharmaceutically acceptable diluents or carriers and other additives and adjuvants may be utilized. Known liquid or solid diluents or carriers and other additives and adjuvants generally used in the art may be properly selected and used. Examples include water, alcohols, various oils and fats of the vegetable or animal origin, various synthetic oils and fats, lactose, starches, dextrin, glucose, sucrose, refined sugar, yeast extracts, yolk, albumin, agar, gelatin, lanolin, millet jelly, glycerol, aluminum hydroxide gel, synthetic aluminum silicate, silicic anhydride, talc, kaolin, barium sulfate, magnesium sulfate, sodium chloride, potassium bromide, potassium iodide, boric acid, magnesium oxide, calcium phosphate, magnesium carbonate, calcium carbonate, sodium hydrogen carbonate, potassium hydrogen carbonate, citric acid, citrate salts, tartaric acid, tartrate salts, potassium hydrogen tartrate, calcium lactate, stearic acid, magnesium stearate, calcium stearate, alginic acid, alkali metal alginates, acetylsalicilic acid, ascorbic acid, ascorbate salts, reduced glutathione, tragacanth gum, gum arabic, methyl cellulose, ethyl cellulose, carboxymethyl cellulose, carboxymethyl cellulose salts, polyvinylpyrrolidone, polyethylene glycol, sorbitan monostearate, fatty acid monoglycerides, and other surface-active agents and emulsifiers. Among them, reducing substances such as ascorbic acid or reduced glutathione are preferred because they further increase the absorption of the iron component of the active ingredient (1) according to the invention. It is also possible to incorporate other pharmaceutical substances such as sedatives, antacids and vitamins, preservatives, stabilizers, sweetenings and flavoring agents into the treating agent of the invention.

Preparation of the compound of formula (1) into compositions in dosage forms can be performed by methods known per se.

The content of the compound of formula (1) in the iron deficiency treating composition of this invention can be properly selected, and is, for example, about 30 to about 95% by weight, based on the total weight of the composition.

The compound of formula (1) according to the invention can be advantageously used for the prevention and therapy of diseases associated with iron deficiency. Specifically, these diseases include, for example, iron deficiency anemia, hypoferremia, hypochromic anemia, hookworm anemia, juvenile anemia, chlorosis, nutritional anemia, achlorhydric anemia and physiological anemia.

The present invention is further illustrated by the following examples.

PRODUCTION EXAMPLE 1

Ferrous sulfate and aluminum sulfate were dissolved in water boiled for about 30 minutes and then saturated with nitrogen by passing nitrogen gas of high purity, to prepare an aqueous solution of ferrous sulfate and aluminum sulfate having an $Fe^{2+}$ concentration of 1.2 mol/liter and an $Al^{3+}$ concentration of 0.6 mol/liter. Separately, sodium hydroxide was dissolved in water pretreated in the same way as above to form an aqueous solution of sodium hydroxide having a concentration of 3 mol/liter. The two solutions were fed in fixed quantities with stirring into a reactor the inside of which was shut out from air; and co-precipitated at a pH of about 8-9 and a temperature of 40° to 42° C. The resultant slurry was filtered in a non-oxidizing atmosphere and then washed with sodium carbonate (0.2 mol/liter) to exchange the $SO_4$ ion with a $CO_3^{2-}$ ion. The product was washed with water and then with ethanol. A part of the product was formed into a suspension by adding water and stored. The remainder was dried in vacuum and stored.

Analysis of the reaction product showed it to have the chemical composition $Fe_4^{2+}Al_2(OH)_{12}CO_3 \cdot 3H_2O$. This compound contained about 37% of divalent iron.

It was ascertained from its powder X-ray diffraction pattern that this compound has a crystal structure similar to hydrotalcite.

PRODUCTION EXAMPLE 2

Aluminum nitrate and ferrous chloride were dissolved in water pre-treated in the same way as in Production Example 1 to prepare an aqueous solution having an $Fe^{2+}$ concentration of 0.6 mol/liter and an $Al^{3+}$ concentration of 0.4 mol/liter. An aqueous solution of sodium hydroxide was prepared in the same way as in Production Example 1.

The two solutions were reacted at a pH of 10 to 10.5 and a temperature of 30° to 32° C. in the same way as in Production Example 1. The product was dehydrated in an atmosphere of an inert gas, washed fully with sodium succinate (0.2 mol/liter), filtered, and dried in vacuum.

The resultant compound was found by chemical analysis to have the composition $Fe_3{}^{2+}Al_2(OH)_{10.4}(CH_2COO)_{1.6}.1.8H_2O$ and contained about 32% of $Fe^{2+}$.

It was ascertained from its powder X-ray diffraction pattern that this compound has a crystal structure similar to hydrotalcite.

PRODUCTION EXAMPLE 3

The same reaction as in Production Example 1 was carried out at a pH of 9 to 9.5 and a temperature of 35° to 40° C. except that the concentrations of $Fe^{2+}$ and $Al^{3+}$ were changed to 0.8 mol/liter and 0.2 mol/liter, respectively. The reaction product was filtered under reduced pressure, washed with water and ethanol, and then dried in vacuum. Chemical analysis showed that part of divalent iron was oxidized, and a compound of the composition $Fe_{5.1}{}^{2+}Al_{1.4}Fe_{0.6}{}^{3+}(OH)_{14.0}(SO_4)_{1.1}.3.2H_2O$ was obtained. The resultant compound contained about 42% of $Fe^{2+}$. It was ascertained from its powder X-ray diffraction pattern that the crystal structure of this compound is the same as hydrotalcite.

PRODUCTION EXAMPLE 4

Magnesium chloride, ferrous sulfate and aluminum chloride were dissolved in water pre-treated in the same way as in Production Example 1 to prepare an aqueous solution having an $Mg^{2+}$ concentration of 0.1 mol/liter, an $Fe^{2+}$ concentration of 0.5 mol/liter and an $Al^{3+}$ concentration of 0.4 mol/liter. Co-precipitation from this solution was carried out in the same way as in Production Example 1 by using sodium hydroxide (3 mols/liter) at a temperature of 50° to 55° C. and a pH of 9 to 9.5. The resultant product was subjected to ion-exchanging using sodium carbonate (0.2 mol/liter). The product was washed with water and methanol, and then dried in vacuum.

Chemical analysis showed the resultant product to have the composition $Fe_5{}^{2+}MgAl_2(OH)_{16}CO_3.4H_2O$ and contain about 44% of $Fe^{2+}$. It was ascertained from its powder X-ray diffraction pattern that the crystal structure of this compound is similar to hydrotalcite.

DRUG FORMULATION EXAMPLE 1

The following ingredients were mixed to form a powder.

| Powder of the compound obtained in Production Example 1 | 500 parts by weight |
|---|---|
| Methyl cellulose | 20 parts by weight |
| Carboxy methyl cellulose | 10 parts by weight |
| Starch | 380 parts by weight |

DRUG FORMULATION EXAMPLE 2

The following ingredients were mixed and continuously tableted under a pressure of about 300 kg/cm² into tablets each weighing 200 mg.

| Powder of the compound obtained in Production Example 1 | 675 parts by weight |
|---|---|
| Carboxy methyl cellulose | 145 parts by weight |
| Starch | 120 parts by weight |
| Vitamin C | 40 parts by weight |
| Magnesium stearate | 20 parts by weight |

DRUG FORMULATION EXAMPLE 3

The following ingredients were uniformly mixed by a homomixer to form a suspension.

| 50% Solution of the compound obtained in Production Example 1 | 800 parts by weight |
|---|---|
| Methylparaben | 0.5 parts by weight |
| Propylparaben | 0.5 parts by weight |
| 70% Sorbitol solution | 11 parts by weight |
| Peppermint | 0.14 parts by weight |
| Flavor | 3 parts by weight |
| Water | 200 parts by weight |

ADMINISTRATION EXAMPLE 1

Test compounds:
(1) 10 ml of a suspension of the compound obtained in Production Example 1 (containing 400 mg of the compound)
(2) 400 mg of dried iron sulfate ($FeSO_4$) and 150 mg of iron fumarate [$Fe(CH-COO)_2$] as controls Test procedure:

Five healthy male volunteers aged between 26 and 46 and weighing between 50 to 65 kg were employed as subjects. On the day of experiment, they were caused to abstain from taking drugs other then the test drugs and such foods as teas and eggs which would adversely affect iron absorption. Breakfast was not given. Lunch was served at 12:30 hours, and supper, after blood letting at 20:30 hours. At 8:30 hours, blood was drawn from the subjects, and immediately then each of the test compounds was administered. After the administration, blood was withdrawn six times at 2, 4, 6, 8 and 12 hours from the administration. A sample of 0.5 ml of serum was taken from each of the bloods. The sample was colored with an Fe-direct reagent, and the generated color was spectrally analyzed at a wavelength of 535 nm to determine the serum iron level of each sample.

Figure 1:
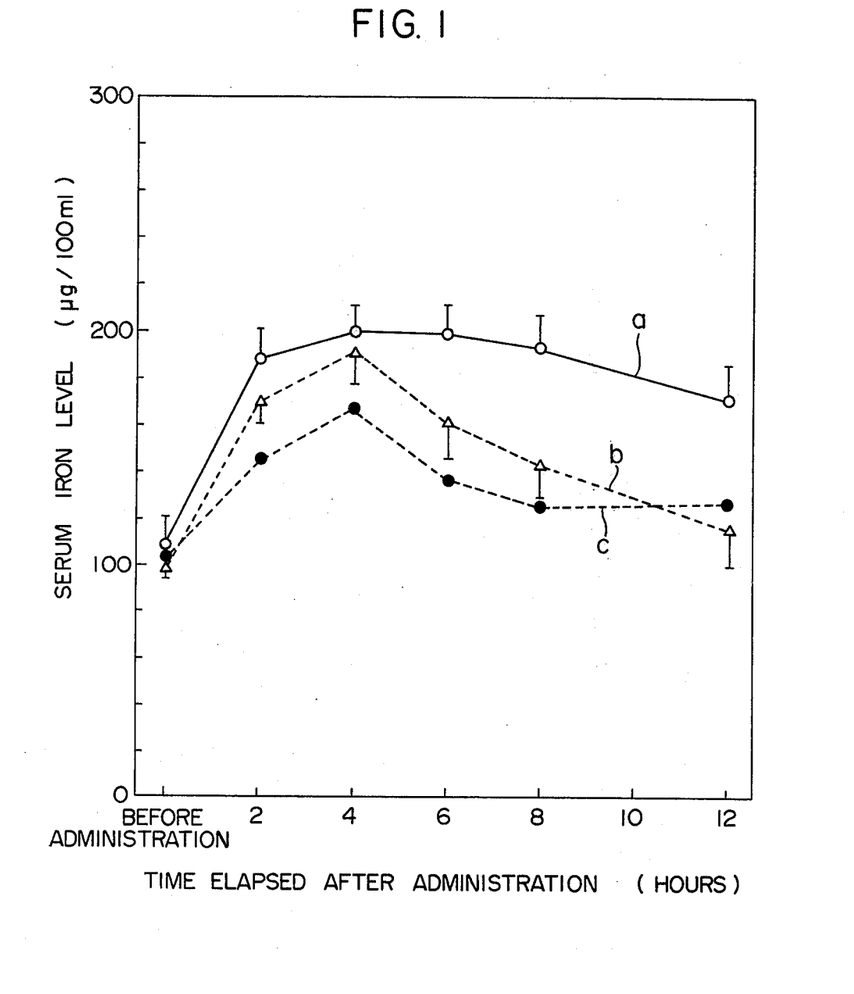

The results obtained are shown in FIG. 1 which is a graph showing the relation between the serum iron level and the time (hours) elapsed after the administration of each of the test compounds. It is seen from FIG. 1 that the treating agent of this invention shows a higher iron absorption than ferrous sulfate heretofore considered to show the highest absorption, and its efficacy is long-lasting. In FIG. 1, the solid line a represents the result obtained with the treating agent of this invention; the dotted line b, the result obtained with ferrous sulfate; and the dotted line c, the result obtained with iron fumarate.

ADMINISTRATION EXAMPLE 2

The reaction procedure of Production Example 1 was repeated except that ferrous chloride and aluminum chloride were used as the starting materials. The reaction product was washed with a 0.2 mol/liter aqueous solution of sodium carbonate in a nitrogen atmosphere to exchange the $Cl^-$ ion with a $CO_3{}^{2-}$ ion. The slurry was hydrothermally treated at 140° C. for 4 hours in an autoclave purged with nitrogen gas. Then, in a hydrogen atmosphere, the product was washed with water, filtered, and then with evacuation, dried at 100° C. for 6 hours. The resulting compound had the composition $Fe_4^{2+}\cdot Al_2(OH)_{12}CO_3\cdot 3H_2O$, was nearly white, and remained stable in the air. It contained 37% of $Fe^{2+}$.

A mixture of 90% of the resultant compound, 9% of carboxy methyl cellulose as a disintegrant and 1% of magnesium stearate as a lubricant was tableted by a rotary tableting machine under a pressure of about 300 kg/cm² to form tablets each having a total weight of 136 mg and containing 50 mg of $Fe^{2+}$.

One tablet was orally administered to each of five volunteers with anemia after breakfast and lunch each day for about one month. The occurrence of side-effects, the amount of hemoglobin in the blood, the serum iron level, and the unsaturated iron binding capacity were examined.

For comparison, 100 mg of dried iron sulfate ($FeSO_4$) was orally administered to each of other five volunteers with anemia after breakfast and lunch each day, and the same items were examined.

The results are shown in Tables 1 and 2.

It is seen from the results that the treating agent of this invention exhibits a high iron absorption in adults with anemia as demonstrated by an increase in the amount of hemoglobin and the serum iron level, and no particular side effects were noted except that light constipation occurred in two subjects. Usually, to completely cure patients with anemia, an iron-containing drug should be administered successively over 1 to 2 months. The treating agent of this invention can fully meet this requirement, and shows good iron absorption with very much reduced side-effects.

On the other hand, iron sulfate heretofore used in treating anemia gave such side-effects as nausea, stomachache, abdominal pain, etc. 2 to 7 days after the start of the administration course, and the administration had to be stopped.

TABLE 1

Iron absorption and side-effects at the time of administering the compound of the invention

| Volunteer | Time of examination (after the start of the administration course) (*) | Hemoglobin (g/dl) | Serum iron (μg/l) | Unsaturated iron-binding capacity (μg/dl) | Side-effects |
|---|---|---|---|---|---|
| A (female) 24 years old | Previous day 7th day 15th day 25th day | 12.4 13.0 13.4 13.9 | 45 144 205 98 | 454 308 213 284 | Tended to have constipation on the 6th day and thereafter; but no other subjective symptoms |
| B (female) 37 years old | Previous day 7th day 15th day 25th day | 13.3 13.3 13.1 13.1 | 98 96 74 83 | 284 287 275 305 | None |
| C (female) 30 years old | Previous day 7th day 15th day 25th day | 10.6 11.9 12.3 13.1 | 33 254 100 96 | 477 216 324 315 | Tended to have constipation on the 9th day and thereafter; but no other subjective symptoms. |
| D (female) 21 years old | Previous day 7th day 15th day 25th day | 6.8 8.2 9.6 12.4 | 20 62 48 96 | 543 531 574 374 | None |
| E (male) 28 years old | Previous day 7th day 15th day 25th day | 15.1 16.3 15.5 16.1 | 115 114 70 116 | 265 262 323 231 | None |

(*): The "previous day" means the day before the start of the administration course.

TABLE 2

Iron absorption and side-effects at the time of administering $FeSO_4$ (a conventional iron-containing drug)

| Volunteer | Time of examination (after the start of the administration course) (*) | Hemoglobin (g/dl) | Serum iron (μg/l) | Unsaturated iron-binding capacity (μg/dl) | Side-effects |
|---|---|---|---|---|---|
| F (female) 28 years old | Previous day 3rd day | 7.5 8.1 | 24 62 | 561 533 | Because of strong nausea on the second day, the administration was stopped on the third day. |
| G (female) 34 years | Previous day 7th day | 12.1 13.0 | 43 144 | 442 308 | Stomachache occurred on the 4th day and thereafter, and |

TABLE 2-continued

Iron absorption and side-effects at the time of administering FeSO₄ (a conventional iron-containing drug)

| Volunteer | Time of examination (after the start of the administration course) (*) | Hemoglobin (g/dl) | Serum iron (μg/l) | Unsaturated iron-binding capacity (μg/dl) | Side-effects |
|---|---|---|---|---|---|
| old | | | | | the administration was stopped on the 6th day. |
| H (female) 19 years old | Previous day 5th day | 9.7 10.6 | 28 33 | 493 477 | Abdominal pain began soon after the administration, and the administration was stopped on the 5th day. |
| I (female) 21 years old | Previous day 4th day | 13.1 13.3 | 102 96 | 273 289 | Because of strong nausea, the administration was stopped on the 4th day. |
| J (male) 32 years old | Previous day 7th day | 16.3 15.5 | 107 115 | 248 265 | Stomachache occurred on the 7th day and thereafter. The administration was stopped on the 7th day. |

(*): The "previous day" means the day before the start of the administration course.

What we claim is:

1. A composition for increasing the iron level in hemoglobin and serum in a subject in need thereof comprising, (1) an amount, effective for increasing said iron level, of a compound having a hydrotalcite-like crystal structure and represented by the following formula (1)

$$(Fe^{2+},Mg^{2+})_x(Al^{3+},Fe^{3+})_2(OH)_{2x+6-n-z}(A^{n-})_z \cdot mH_2O \qquad (1)$$

wherein $A^{n-}$ represents an anion having a valence of n, $Mg^{2+}$ is within the range of $0 \leq Mg^{2+} < x$, $Fe^{3+}$ is within the range of $0 \leq Fe^{3+} < 2$, x is a number represented by $1 \leq x < 20$, z is a number represented by $0 < z < 3$, and m is a number represented by $0 \leq m < 8$, and (2) a pharmaceutically acceptable diluent or carrier.

2. The composition of claim 1 wherein said compound (1) is represented by the following formula $$(Fe^{2+})_x(Al^{3+})_2(OH)_{2x+6-2z}(CO_3^{2-})_z \cdot mH_2O$$

wherein x, z and m are as defined in claim 1.

3. The composition of claim 1 or 2 wherein x is a number represented by $2.5 \leq x < 8$.

4. The composition of claim 1 wherein $A^{n-}$ is an anion selected from the group consisting of $CO_3^{2-}$, $SO_4^{2-}$, $OH^{-1}$, $(CHOHCOO)_2^{2-}$, $(CHOH)_4CH_2OHCOO^{1-}$, $C_2H_2(COO)_2^{2-}$, $(CH_2COO)_2^{2-}$, $C_5H_9O_5COO^{1-}$ and $CH_3CHOHCOO^{1-}$.

5. The composition of claim 1 wherein the amount of the compound (1) is about 30 to about 95% based on the total weight of the composition.

6. The composition of claim 1 wherein said compound (1) is obtained by reacting an aqueous solution of a water-soluble divalent iron salt or an aqueous solution of a water-soluble divalent iron salt and a water-soluble magnesium salt with an aqueous solution of a water-soluble aluminum compound or an aqueous solution of a water-soluble aluminum compound and a water-soluble trivalent iron salt in the presence of an alkali.

7. A method for, increasing the iron level of hemoglobin and serum in a subject in need thereof, which comprises orally administering an amount, effective for increasing said iron level, of a compound having a hydrotalcite-like crystal structure and represented by the following formula $$(Fe^{2+},Mg^{2+})_x(Al^{3+},Fe^{3+})_2(OH)_{2x+6-n-z}(A^{n-})_z \cdot mH_2O$$

wherein $A^{n-}$ represents an anion having a valence of n, $Mg^{2+}$ is within the range of $0 \leq Mg^{2+} < z$, $Fe^{3+}$ is within the range of $0 \leq Fe^{3+} < -2$, x is a number represented by $1 \leq x < 20$, z is a number represented by $0 < z < 3$, and m is a number represented by $0 \leq m - 8$.

8. The method of claim 7 wherein said compound is represented by the following formula $$(Fe^{2+})_x(Al^{3+})_2(OH)_{2x+6-2z}(CO_3^{2-})_z \cdot mH_2O$$

wherein x, z and m are as defined in claim 7.

9. The method of claim 7 or 8 wherein the dosage of the compound is about 50 mg to about 2,000 mg per day per adult.

10. The method of claim 9 for treating a patient suffering from anemic symptoms.

11. The method of claim 10 for increasing the hemoglobin level of a patient suffering from iron deficiency anemia.

12. The method of claim 9 wherein the compound is administered to a patient suffering from hypoferremia.

13. The method of claim 9 wherein x is a number represented by $2.5 \leq x < 8$ and z is a number represented by $1 \leq z \leq 2$.

14. The composition of claim 3 wherein z is a number represented by $1 \leq z \leq 1$.

15. The composition of claim 1 wherein the compound (1) has the formula $Fe_4^{2+}Al_2(OH)_{12}CO_3 \cdot 3H_2O$.

16. The composition of claim 1 wherein the compound (1) has the formula $Fe_3^{2+}Al_2(OH)_{10.4}(CH_2COO)_{1.6} \cdot 1.8H_2O$.

17. The composition of claim 1 wherein the compound (1) has the formula $Fe_{5.1}^{2+}Al_{1.4}Fe_{0.6}^{3+}(OH)_{14.0}(SO_4)_{1.1} \cdot 3.2H_2O$.

18. The composition of claim 1 wherein the compound (1) has the formula $Fe_5^{2+}MgAl_2(OH)_{16}CO_3 \cdot 4H_2O$.

* * * * *

UNITED STATES PATENT AND TRADEMARK OFFICE
CERTIFICATE OF CORRECTION

PATENT NO. : 4,415,555
DATED : November 15, 1983
INVENTOR(S) : Hitoshi Anabuki and Shigeo Miyata It is certified that error appears in the above—identified patent and that said Letters Patent is hereby corrected as shown below:

Claim 7, column 12, line 45, should read as follows:
within the range of $0 \leq Fe^{3+} < 2$, x is a number repre- Signed and Sealed this Sixth Day of March 1984

[SEAL]

Attest:

GERALD J. MOSSINGHOFF

Attesting Officer  Commissioner of Patents and Trademarks

UNITED STATES PATENT AND TRADEMARK OFFICE
CERTIFICATE OF CORRECTION

PATENT NO. : 4,415,555
DATED : November 15, 1983
INVENTOR(S) : HITOSHI ANABUKI, ET AL.

It is certified that error appears in the above-identified patent and that said Letters Patent is hereby corrected as shown below:

Please correct the Assignee to read as follows:

--- Kyowa Chemical Industry Co., Ltd. ---

Signed and Sealed this

Eleventh Day of September 1984

[SEAL]

Attest:

GERALD J. MOSSINGHOFF

Attesting Officer

Commissioner of Patents and Trademarks